US012193408B2

(12) United States Patent
Coletti et al.

(10) Patent No.: US 12,193,408 B2
(45) Date of Patent: Jan. 14, 2025

(54) PET HEALTH AND IDENTIFICATION MANAGEMENT SYSTEM

(71) Applicant: GLOBAL PET SECURITY, LLC, Sugarcreek, OH (US)

(72) Inventors: Phillip Coletti, Strasburg, OH (US); Paul Miller, Sugarcreek, OH (US)

(73) Assignee: GLOBAL PET SECURITY, LLC

( * ) Notice: Subject to any disclaimer, the term of this patent is extended or adjusted under 35 U.S.C. 154(b) by 156 days.

(21) Appl. No.: 18/160,769

(22) Filed: Jan. 27, 2023

(65) Prior Publication Data

US 2024/0251753 A1 Aug. 1, 2024

(51) Int. Cl.
| | |
|---|---|
| *G08B 23/00* | (2006.01) |
| *A01K 11/00* | (2006.01) |
| *G06F 16/9035* | (2019.01) |
| *G16H 10/60* | (2018.01) |

(52) U.S. Cl.
CPC ........ *A01K 11/006* (2013.01); *G06F 16/9035* (2019.01); *G16H 10/60* (2018.01)

(58) Field of Classification Search
CPC ... A01K 11/006; G06F 16/9035; G16H 10/60
See application file for complete search history.

(56) References Cited

U.S. PATENT DOCUMENTS

| | | | | |
|---|---|---|---|---|
| 2003/0204417 A1* | 10/2003 | Mize | ...................... | G16H 10/60 |
| | | | | 705/14.69 |
| 2016/0063188 A1* | 3/2016 | Thornberry | ............. | H04L 63/08 |
| | | | | 705/3 |
| 2018/0098523 A1 | 4/2018 | Basom | | |
| 2024/0090472 A1* | 3/2024 | Bishop | ................. | A01K 29/005 |

FOREIGN PATENT DOCUMENTS

| | | |
|---|---|---|
| CN | 108038189 A | 5/2018 |
| KR | 20030096933 A | 12/2003 |
| KR | 20070081610 A | 8/2007 |
| KR | 20080094117 A | 10/2008 |

\* cited by examiner

*Primary Examiner* — Toan N Pham
(74) *Attorney, Agent, or Firm* — Emerson Thomson Bennett; Daniel A. Thomson

(57) ABSTRACT

Provided herewith is a system for recording and transmitting pet information. A server maintains a plurality of web-accessible documents and services including a pet profile, which includes editable fields for entering and maintaining specific categories of information about a pet. Shareable specialty profiles of the pet profile each display a specialty subset of the specific categories to respective specialty pet servicing personnel. Specialty web access portals each provide read and write access of a respective shareable specialty profile to the personnel. A shareable public profile of the pet profile displays a public portion of the categories on a publicly accessible web page. A scannable code enables a public user to access the web page including the shareable public profile from the server upon scanning with a handheld mobile device. A wireless communication system transmits the public profile from the server to the mobile device.

15 Claims, 3 Drawing Sheets

PET HEALTH AND IDENTIFICATION MANAGEMENT SYSTEM

I. BACKGROUND

A. Technical Field

The present disclosure pertains to the art of domestic animal tracking, management, and healthcare. Specifically, this disclosure teaches a QR code system, and attendant multi-function application platform, for managing the identification and healthcare of pets and other domesticated animals.

B. Description of Related Art

Animal owners, generally, are constantly seeking new ways to care for and manage their animals. Pet owners, in particular, face issues with lost pets and pet medical problems. This has given rise to numerous interfaces and support systems used to protect animals and allow owners to more closely monitor, interact with, and reclaim their animals.

Physical tags have been implemented in the past. These tags contain standard pet information, such as name, breed, and address, engraved on the tag itself. The information contained on these tags, however, is very limited and provides no means of identification, location, or recovery beyond such minor details.

Microchipping technology attempts to remedy many of these ills using an embedded chip within the animal to relay information and data. These systems can contain more information than a physical tag or GPS tracker and can be used to locate the pet.

There have been attempts in the past to address many of the issues raised by those various technologies. For example, U.S. patent Application Publication 2018/0098523 A1 discloses "a system for owners of domestic animals whereby a single authorized smart rabies tag immediately and in real-time provides pet information to a mobile device through a QR code located on the rabies tag . . . single Smart Rabies Tags [that] provide comprehensive pet information including health care data and allow real-time access for locating lost pets . . . system also includes access through an individual pet website." See U.S. Patent Application Publication 2018/0098523 A1. However, that form of QR code interface is too limited in function. There are several quality-of-life and convenience features that the above system lacks. Features that would otherwise allow for greater engagement between pets, pet owners, and veterinarians. The system embodied by the present invention addresses that issue by disclosing a QR code and mobile application system that provides a host of practical and quality-of-life functions for both pet owners and veterinarians.

Of highest priority to pet owners is ease of access to vital information about the animal, as well as a means of locating, monitoring, and recovering the pet reliably and across great distances. The system described resolves these issues using a QR-enabled tag, which allows interface with a profile and mobile application platform containing location tracking, alerts, and access to extensive information about the pet. The application platform also introduces such features as local and remote document and record storage, means for instantaneously transferring and sharing those documents, live-chat support for interaction between veterinarians and owners, and a variety of informational and training videos covering a host of important topics for pet owners.

Overall, the invention described allows seamless interaction between pets, owners, and veterinarians through a multi-function platform designed specifically to maximize engagement and access.

II. SUMMARY

Provided in this disclosure is a system for recording and transmitting pet information. A server is provided for maintaining a plurality of web-accessible documents and services. A pet profile is one of the documents on the server and includes a plurality of editable fields for entering and maintaining specific categories of information about a pet. The pet profile includes one or more shareable specialty profiles, for displaying a specialty subset of the specific categories of information about the pet to respective specialty pet servicing personnel. One or more specialty web access portals provide read and write access of a respective shareable specialty profile to the respective specialty pet servicing personnel. The pet profile also includes a shareable public profile for displaying a public portion of the specific categories of information about the pet on a publicly accessible web page. A scannable code enables a public user to access the web page including the shareable public profile from the server upon scanning with a hand-held mobile device. A wireless communication system transmits the shareable public profile from the server to the hand-held mobile device of the public user.

In the present system, the specialty pet servicing personnel can include individuals having different fields of pet expertise. The specialty subset of the shareable specialty profiles can include specific categories of information about the pet relevant to a respective field of expertise. These respective fields of expertise can include pet grooming, pet veterinary treatment, pet competition, or any other field relating to pets and their care.

In the present system, the specialty web access portals can include an email service for sending and receiving the respective shareable specialty profile between the server and the specialty pet servicing personnel. The server includes a data extraction tool for automatically extracting information from an email received from the specialty pet servicing personnel and automatically entering the information into suitable editable fields of the specific categories of information about the pet in the pet profile.

The present system also includes a profile creation portal for creating initial data entries into the plurality of editable fields for entering and maintaining the specific categories of information about the pet. The profile creation portal can include a breeder portal, a pet broker portal, and/or a pet store portal for enabling pet distribution entities to create or add to the initial data entries for the pet profile. The profile creation portal can also include a retail portal for enabling a pet owner to access the server to create and activate a new pet profile. The profile creation portal can also include an administrative portal for server-side access to create, activate and maintain a new pet profile.

In other aspects of the present system, the scannable code is preferably incorporated into an identification tag affixed to a pet collar. A notification tool can be provided in communication with the server for sending a notification to a pet owner when the scannable code is accessed by the public user. An app service can include optional subscription services. A services portal can provide access to the optional subscription services which can include online chat/virtual with pet professionals, including veterinarians and trainers. An alert component is provided in communication with the server for enabling a pet owner to notify users in communication with the server of a missing pet within a predetermined radius. An interface can be provided in communication with the server for integrating the pet profile with a pet microchip registry database.

According to an aspect, the present invention provides a new and improved approach to organizing and disseminating information about a pet.

According to another aspect, the present invention provides a new and improved approach to identification, location, and recovery of a lost pet.

According to still another aspect, the present invention provides an inexpensive and readily accessible approach to identification, location, and recovery of a lost pet.

According to yet another aspect, the present invention provides for greater engagement between pets, pet owners, and veterinarians.

According to a further aspect, the present invention provides practical and quality-of-life functions for both pet owners and veterinarians.

Other benefits and advantages of this invention will become apparent to those skilled in the art to which it pertains upon reading and understanding of the following detailed specification.

III. BRIEF DESCRIPTION OF THE FIGURES

The above drawings form part of the disclosure and specification and are included to further demonstrate certain aspects of the invention, which aspects will be described in detail later in this specification. The invention may be better understood by reference to these drawings in conjunction with the detailed description.

IV. DETAILED DESCRIPTION

Figure 1:
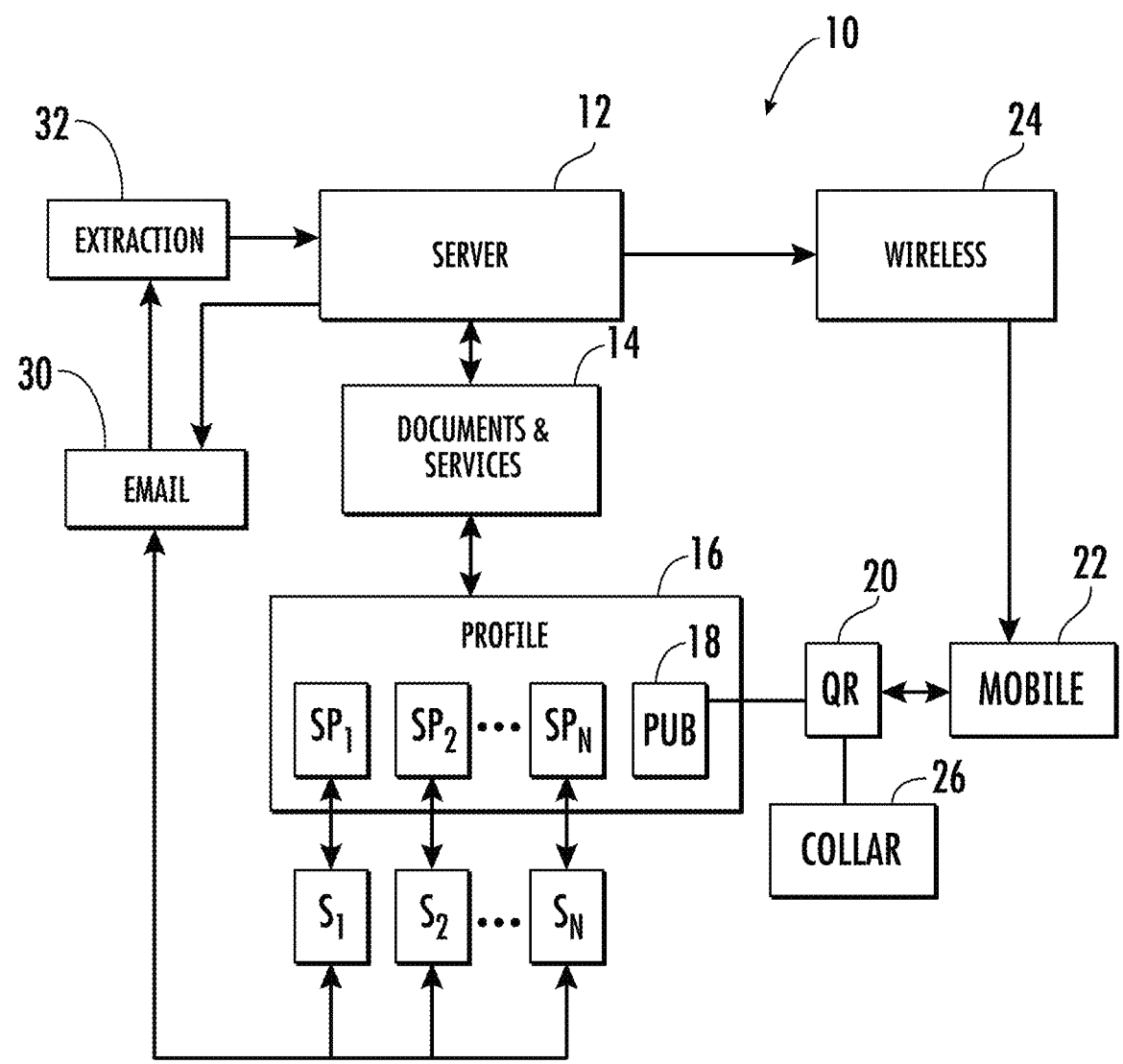
FIG. 1 is a flow chart illustrating the general structure of a system in accordance with the present invention.

Reference is now made to the drawings wherein the showings are for purposes of illustrating embodiments of the article only and not for purposes of limiting the same, and wherein like reference numerals are understood to refer to like components.

FIG. 1 depicts a system 10 for recording and transmitting pet information. The present system 10 enables animal owners to access pet information and location data, as well as several helpful and convenient functions. The system 10 includes an application platform implemented on a server 12 for maintaining a plurality of web-accessible documents and services 14. The documents 14 include a pet profile 16 which itself includes a plurality of editable fields for entering and maintaining specific categories of information about a pet. For example, the pet profile 16 can include fields regarding the pet's name, breed, physical description, complete medical history, microchip number (if applicable), etc. Alternatively, the pet profile 16 can also include links to discrete document and record files pertaining to the pet's medical history, grooming visits, pet show competitions, and other attributes.

With continued reference to FIG. 1, the pet profile 16 includes a plurality of shareable specialty profiles $SP_1$, $SP_2$ . . . $SP_N$ for each displaying a specialty subset of the specific categories of information about the pet relevant to respective specialty pet servicing personnel. The system 10 also includes a respective plurality of specialty web access portals $S_1$, $S_2$ . . . $S_N$ for each of the specialty profiles $SP_1$, $SP_2$ . . . $SP_N$, for providing read and write access of a respective shareable specialty profile to the respective specialty pet servicing personnel. The portals $S_1$, $S_2$ . . . $S_N$ enable the personnel to access and download the respectively associated specialty profiles to obtain any necessary information about the pet prior to an interaction, and to upload updated information to the specialty profile after the interaction is completed.

With further reference to FIG. 1, the specialty pet servicing personnel represent different fields of pet expertise. The specialty subset of each shareable specialty profile includes specific categories of information about the pet relevant to a respective field of expertise. These respective fields of expertise include pet grooming, pet veterinary treatment, or pet competition. As such, the shareable specialty profiles $SP_1$, $SP_2$ . . . $SP_N$ can include veterinary, grooming, pet show organizations, or any other categories of information that pertain to the pet, and the personnel can be any professionals associated with these profiles, as will be described hereinbelow in connection with FIG. 3. For example, a veterinarian can retrieve a pet's health records before an examination and add information about any diagnosis, medications, surgeries, etc. A veterinary specialty profile can be retrieved via a mobile application platform on a smartphone or via a website associated with the system 10. Each of the portals $S_1$, $S_2$ . . . $S_N$ can be implemented by a series of respective specialty mobile phone applications to access web-enabled documents, or they can be accessed by suitable webpages in a conventional web browser.

Figure 3:
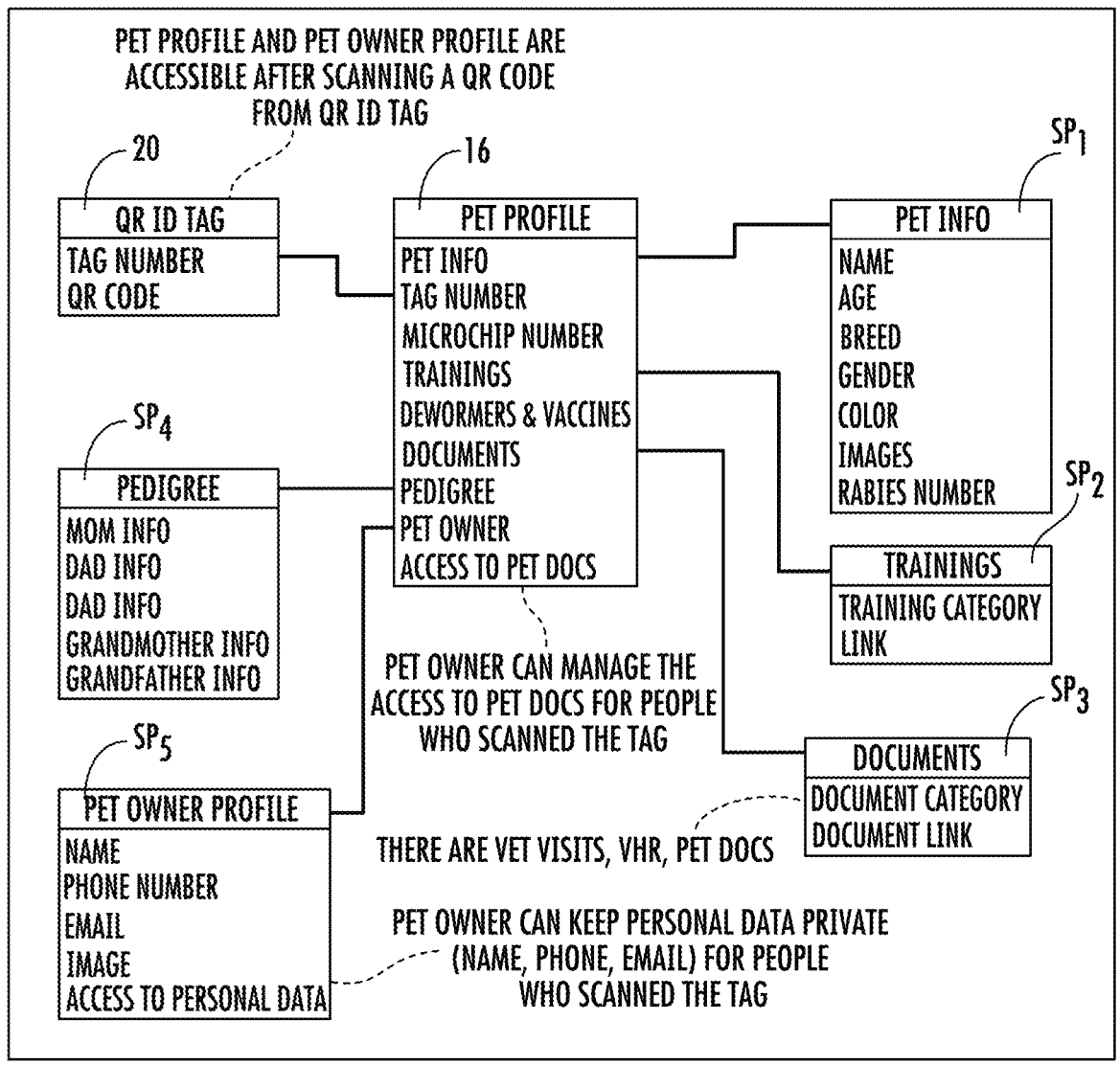
FIG. 3 is a flow chart depicting several types of specialty profiles used in a pet profile in accordance with the system shown in the flow chart of FIG. 1.

With reference to FIG. 3, the pet profile 16 includes profile information incorporated from the respective shareable specialty profiles $SP_1$, $SP_2$ . . . $SP_N$. Access to this information can be managed by the pet owner, who can determine what information is accessible by various persons who scan the QR code 20. In one exemplary implementation, a tag number from the QR code 20 tag can be included. A specialty profile $SP_1$ can include pet information, such as a pet's name, age, breed, gender, color, image(s), and rabies vaccine number. A specialty profile $SP_2$ can include a pet's trainings such as a training category and a link to an online certification document. A specialty profile $SP_3$ can include various documents related to the pet such as veterinarian visits, VHR, etc., grouped according to category, with copies of the documents themselves or links to online documents. A specialty profile $SP_3$ can include pedigree information, including the names and information pertaining to the animal's parents and grandparents. A specialty profile $SP_4$ can include a pet owner profile including the name, phone number, email address, image(s), and other personal data associated with the pet owner. Any other configuration of specialty profiles and associated information could also be contemplated without departing from the invention.

As additionally shown in FIG. 1, the specialty web access portals $S_1$, $S_2$ . . . $S_N$ interface with an email service 30 for sending and receiving the respective shareable specialty profiles $SP_1$, $SP_2$ . . . $SP_N$ between the server 12 and the specialty pet servicing personnel. In one aspect, the email service 30 can include an email domain such as Google Suites, though any suitable service can be contemplated without departing from the invention. The server 10 includes a data extraction tool 32 for automatically extracting information from an email received from the specialty pet servicing personnel and automatically entering the information into suitable editable fields of the specific categories of information about the pet in the pet profile 16. In this manner, veterinarians, groomers, and other pet professionals can provide real-time updates to the profile 16 following an interaction. The email service 30 can generate a unique email address for each scannable QR code 20 in the system 10 associated with an individual pet, or else a plurality of scannable CR codes 20 for a plurality of pets can be sent via the same email address and sorted according to an account number in the email header associated with the pet's QR code 20.

With ongoing reference to FIG. 1, the system 10 also includes a shareable public profile 18 of the pet profile, for displaying a public portion of the specific categories of information about the pet on a publicly accessible web page. This public portion can include the pet's name and a photo of the pet, along with a name and contact information of the pet's owner. A scannable code 20 is associated with the public profile 18 for enabling a public user to access the web page including the shareable public profile 18 from the server 12 upon scanning with a hand-held mobile device 22, such as a smartphone. The scannable code 20 connects the mobile device 22 to the server 12 via a wireless communication system 24, which can be a cellular network, Wi-Fi system or Bluetooth connection by which the mobile device 22 is connected to the internet. The wireless communication system 24 transmits the detected scannable code 20 over the internet to the server 12, which sends the shareable public profile 18 back from the server 12 to the hand-held mobile device 22 of the public user.

As also generally depicted in FIG. 1, the scannable code 20 is preferably incorporated into an identification tag affixed to a pet collar 26. Preferably, the scannable code 20 is a QR (quick response) code. The QR code 20 is linked to a web page associated with the public profile 18 of the specific pet to which the code is registered, on both a website and within an application platform of the present system 10. The QR code 20 can be scanned by any mobile device 22, which will then show the pet owner's information, so the pet can be reunited with its owner.

Figure 2:
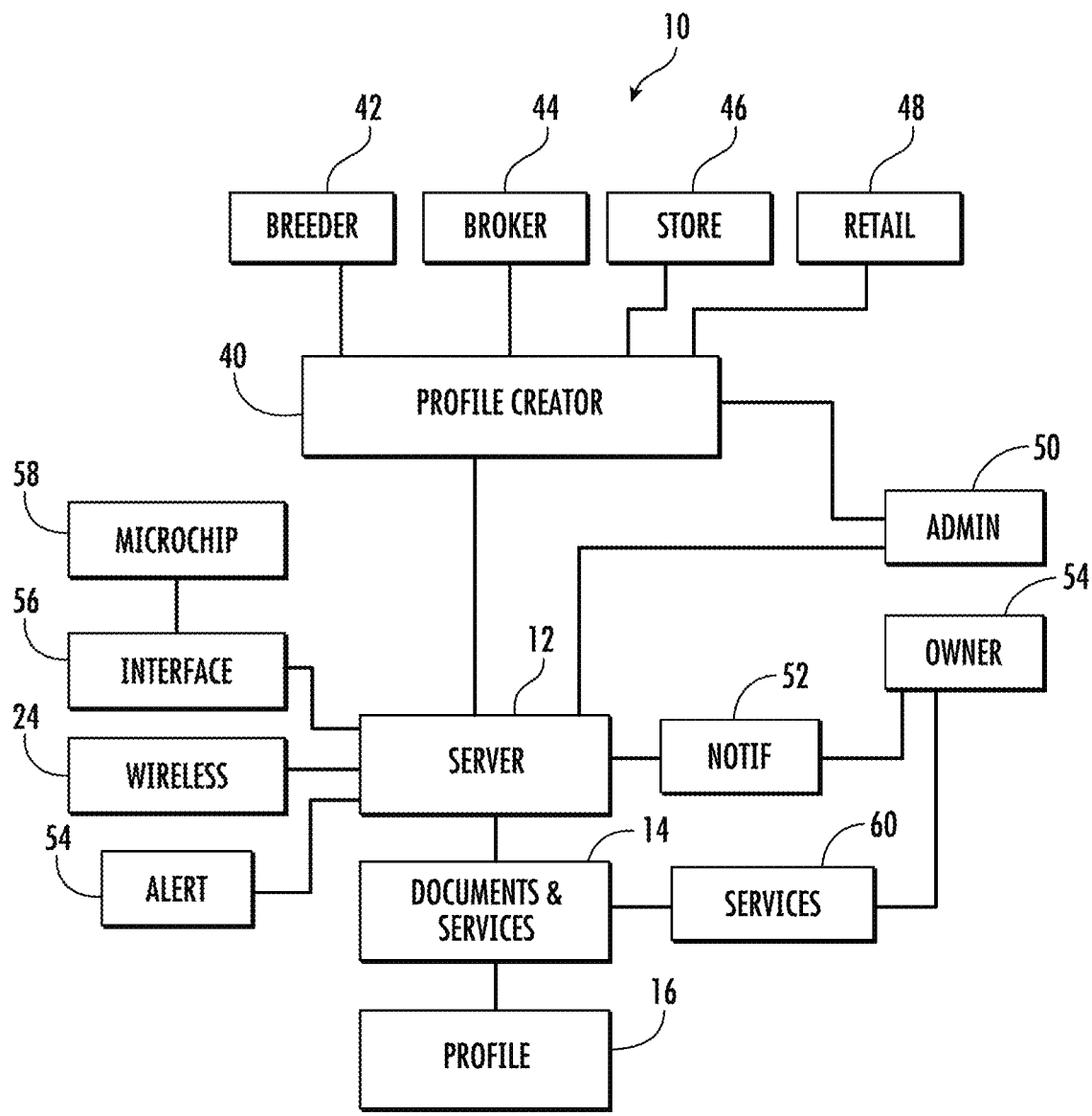
FIG. 2 is a flow chart illustrating various additional functionality and uses of the multi-function application platform, tied to the specific pet through the QR code tag and system.

Turning now to FIG. 2, the application platform of the system 10 additionally includes a profile creation portal 40 for creating initial data entries into the plurality of editable fields of the pet profile 16. The profile creation portal 40 can be used by a plurality of pet distribution entities for creating a profile 16 and/or adding to the initial data entries for the pet profile 16, for entering and maintaining the specific categories of information about the pet. For example, the profile creation portal 40 can includes a breeder portal 42 so that the pet profile 16 can be created at birth by the pet breeder, who can record early medical information and other data about the pet. This profile 16 can then be handed off to a pet broker, using a broker portal 44, who can enter additional medical and other information about the pet to the profile 16 after leaving the breeder. A pet store portal 46 can then be used to enable pet store personnel to receive the profile 16 from the broker and enter additional pet data into the profile 16, which can then be handed off to the pet owner upon taking possession of the pet.

With continued reference to FIG. 2, the profile creation portal 40 can also include a retail portal 48 for enabling a pet owner to access the server 12 to create and activate a new pet profile 16. The pet owner can purchase a tag having a scannable QR code 20 at a retail store. The tag with the code 20 is associated with a "freelance" profile that can be activated and created by the owner. The owner can scan the code 20 with a mobile device 22, which opens a phone app into which data can be entered, which is then forwarded back to the server 12 via the email service 30, whereupon the editable fields of the profile 16 are populated by the server 12 using information obtained through the extraction tool 32. After downloading the App and creating a personal profile, the pet owner can "ADD A PET." The owner can scan the code 20 within the "Add a pet" option inside the app, which opens the pet profile into which data can be entered, which is then forwarded back to the server 12 via the email service 30, whereupon the editable fields of the profile 16 are populated by the server 12 using information obtained through the extraction tool 32.

With ongoing reference to FIG. 2, the profile creation portal 40 can also include an administrative portal 50 for server-side access to create, activate and maintain a new pet profile 16. This can be done as a service to a pet owner performed by an administrator of the system 10, who can then subsequently deliver a tag including a scannable QR code to the pet owner. The administrative portal 50 can also access the server 12 to provide any additional administrative functions, including updating and maintaining a profile 16 and performing server-side administration of any other functionality of the system 10. The administrative portal 50 receives orders, sends invoices, sends tag id numbers, can edit pet profiles, and tracks what "Connect portals 42, 44, 46, and 48" order sell and transfer. The administrative portal 50 can also receive orders from the app and edit pet profiles from pet owners/app users.

With further reference to FIG. 2, the application platform of the system 10 includes a notification tool 52 in communication with the server 12 for sending a notification to a pet owner 52 when the scannable QR code 20 is accessed by the mobile device 22 of a public user. The notification can be sent to the mobile device of the pet owner 52 via the wireless communication system 24. Scanning the QR code 20 transmits GPS coordinates from the server 12 via text and/or a notification in the application platform to the pet owner 52 including the current whereabouts of the pet, so that the pet can be reunited with the owner.

With additional reference to FIG. 2, the system 10 also includes an alert component 54 in communication with the server 10 for enabling a pet owner to notify users in communication with the server 10 of a missing pet within a predetermined radius. The alert component 54 can instruct the server 12 to send a text and/or an application notification to any subscribers of the application platform within a selected area having a predetermined radius around the last known whereabouts of the missing pet. The notification can include a name, description, or picture of the pet, and/or a link to the public profile 18, to enable others within the radius to identify the pet and facilitate reuniting with the owner 52. The system 10 can also include an interface 56 in communication with the server 12 for integrating the pet profile 16 with a pet microchip registry database 58, which can be further useful for identifying and retrieving a missing pet. In one aspect, the interface 58 can be integrated with the microchip registry database of the American Animal Hospital Association (AAHA) to link the microchip lookup with the pet profile 16. However, any suitable database 58 could be employed without departing from the invention.

As still further depicted in FIG. 2, the web-accessible documents and services 14 of the application platform of the system 10 can include optional subscription services. The system 10 includes a services portal 60 for obtaining access to the optional subscription services. These optional services can include proprietary digital content such as articles and videos of relevance to a pet's breed, medical history, dietary requirements, etc. The services can also include live online chat with pet service providers, such as veterinarians, trainers, and various expert professionals. These optional services can be obtained for an additional cost over and above access to the application platform of the system 10.

As disclosed herewith and depicted in FIGS. 1 and 2, the remote server 12 provides storage and data management for the pet profile 16 and the corresponding website of the application platform, and the system 10 includes local management functions and storage capabilities for files and other important documents on a mobile device of the pet owner. Information and files can be retrieved from the remote server to store on the application platform of the mobile device and can be interchangeably sent to the server and website from the application's local storage. Third parties that scan the QR code 20 can access the public profile 18 from the remote server. One embodiment of this invention provides for differing degrees of access, depending on the classification of the third party involved. For example, a set of credentials—to be supplied after QR code scanning—could differentiate an approved veterinarian or pet healthcare company professional from an otherwise unassociated third party. Such differentiation could provide more in-depth information for those approved parties, while safeguarding any pet information the owner wishes to keep private.

As disclosed herewith and depicted in FIGS. 1 and 2, the present invention provides an array of features and functions embodied by the mobile application platform. The present application platform on the server 12 can also provide email and text alerts of important appointments and deadlines for pets and pet owners. Using the mobile application, a pet owner or approved veterinarian can set appointments for healthcare visits, medication dosage, feeding, and any other important events. The system then sends notification emails and texts to the owner 52, reminding them of these events. The application system can also allow for real-time transfer of medical documents, pictures, and other files between users of the platform or website. An owner may use a "Share Now" feature to send files to veterinarians' email address or application. Similarly, a file sent or received via email can be transferred to the application platform, for local storage or to the website pet profile. The application platform also supports live-chat functionality. Pet owners and veterinarians may access video chat features within the application to enable face-to-face interaction and coordination. When using the live-chat function, the QR code 20 can indicate to the receiving party the specific pet about which the live-chat pertains, and access to both the pet profile and "Share Now" features allow owners and veterinarians to send and receive important documents and medical information. The optional subscription content can also include a variety of informational videos regarding pet training, safety, health, and other important topics and frequently asked questions, which can be accessed through their mobile device. One embodiment of this invention provides for personalized video recommendations, proffered by either a machine learning algorithm or veterinarian, through the pet profile. Such recommendations then would be visible from the pet profile on the application or website, unique to that pet profile, and responsive to the pet and their needs.

Overall, the present system 10 and associated application platform provide a central hub for all relevant information about the specific pet, a means of easily locating and recovering them should they become lost, and tools for owners to promptly coordinate and engage with veterinarians, all keyed to the animal's personal profile.

Optionally, the present system can include a GPS device for linking to the pet profile so that the user can buy the device and pay a subscription and have real time location and tracking of the pet. The GPS device links to the pet profile as an added tracking option for the profile linked to a QR Code. The QR Code is printed on the device for back up in case of dead batteries. The user can control the GPS devise via the app with numerous different settings for safe zones, step count, heartbeat monitoring and more.

Numerous aspects have been described, hereinabove. It will be apparent to those skilled in the art that the above methods and apparatuses may incorporate changes and modifications without departing from the general scope of the present disclosure. It is intended to include all such modifications and alterations in so far as they come within the scope of the appended claims or the equivalents thereof.

What is claimed:

1. A system for recording and transmitting pet information, comprising:
   a server for maintaining a plurality of web-accessible documents and services;
   a pet profile comprising a plurality of editable fields for entering and maintaining specific categories of information about a pet, wherein the plurality of web-accessible documents on the server comprises the pet profile;
   at least one shareable specialty profile of the pet profile, for displaying a specialty subset of the specific categories of information about the pet to respective specialty pet servicing personnel;
   at least one specialty web access portal for providing read and write access of a respective shareable specialty profile to the respective specialty pet servicing personnel;
   a shareable public profile of the pet profile, for displaying a public portion of the specific categories of information about the pet on a publicly accessible web page;
   a scannable code for enabling a public user to access the web page including the shareable public profile from the server upon scanning with a hand-held mobile device; and
   a wireless communication system for transmitting the shareable public profile from the server to the hand-held mobile device of the public user.

2. The system of claim 1, wherein the specialty pet servicing personnel comprise different fields of pet expertise, and wherein the specialty subset of the at least one shareable specialty profile comprises specific categories of information about the pet relevant to a respective field of expertise.

3. The system of claim 2, wherein the respective fields of expertise comprise at least one of pet grooming, pet veterinary treatment, or pet competition.

4. The system of claim 1, wherein the at least one specialty web access portal comprises an email service for sending and receiving the respective shareable specialty profile between the server and the specialty pet servicing personnel.

5. The system of claim 4, wherein the server further comprising a data extraction tool for automatically extracting information from an email received from the specialty pet servicing personnel and automatically entering the information into suitable editable fields of the specific categories of information about the pet in the pet profile.

6. The system of claim 1, further comprising a profile creation portal for creating initial data entries into the plurality of editable fields for entering and maintaining the specific categories of information about the pet.

7. The system of claim 6, wherein the profile creation portal further comprises at least one of a breeder portal, a pet broker portal, or a pet store portal for enabling pet distribution entities to create or add to the initial data entries for the pet profile.

8. The system of claim 6, wherein the profile creation portal further comprises a retail portal for enabling a pet owner to access the server to create and activate a new pet profile.

9. The system of claim 1, wherein a profile creation portal further comprises an administrative portal for server-side access to create, activate and maintain a new pet profile.

10. The system of claim 1, wherein the scannable code is incorporated into an identification tag affixed to a pet collar.

11. The system of claim 1, further comprising a notification tool in communication with the server for sending a notification to a pet owner when the scannable code is accessed by the public user.

12. The system of claim 1, wherein the web-accessible documents and services comprises optional subscription services and wherein the system further comprises a services portal for providing a pet owner with access to the optional subscription services.

13. The system of claim 12, wherein the optional services comprise online chat with pet service providers.

14. The system of claim 1, further comprising an alert component in communication with the server for enabling a pet owner to notify users in communication with the server of a missing pet within a predetermined radius.

15. The system of claim 1, further comprising an interface in communication with the server for integrating the pet profile with a pet microchip registry database.

* * * * *